(12) United States Patent  (10) Patent No.: US 7,712,379 B2
Abu-Farha et al.  (45) Date of Patent: May 11, 2010

(54) UNIAXIALLY-DRIVEN CONTROLLED BIAXIAL TESTING FIXTURE

(75) Inventors: Fadi Abu-Farha, Lexington, KY (US); Marwan Khraisheh, Lexington, KY (US)

(73) Assignee: The University of Kentucky Research Foundatio, Lexington, KY (US)

( * ) Notice: Subject to any disclaimer, the term of this patent is extended or adjusted under 35 U.S.C. 154(b) by 77 days.

(21) Appl. No.: 12/120,500

(22) Filed: May 14, 2008

(65) Prior Publication Data

US 2009/0282929 A1  Nov. 19, 2009

(51) Int. Cl.
 G01N 3/02  (2006.01)
(52) U.S. Cl. .................................. 73/856; 73/862.041
(58) Field of Classification Search ........... 73/856–865, 73/862.041–862.046
See application file for complete search history.

(56) References Cited

U.S. PATENT DOCUMENTS

| | | | |
|---|---|---|---|
| 3,807,224 A | 4/1974 | Hassenboehler | |
| 4,448,083 A * | 5/1984 | Hayashi ................. | 73/862.042 |
| 4,567,774 A | 2/1986 | Manahan et al. | |
| 4,582,990 A * | 4/1986 | Stevens ...................... | 250/328 |
| 4,677,854 A | 7/1987 | Gabelli | |
| 4,814,622 A * | 3/1989 | Gregory et al. ............... | 850/18 |
| 4,825,700 A * | 5/1989 | Vardoulakis et al. .......... | 73/749 |
| 5,063,785 A | 11/1991 | Labuz et al. | |
| 5,144,844 A | 9/1992 | Mathiak et al. | |
| 5,186,043 A * | 2/1993 | Yamaoka et al. ......... | 73/117.03 |
| 5,279,166 A | 1/1994 | Ward et al. | |
| 5,448,918 A | 9/1995 | Tucchio | |
| 5,706,027 A * | 1/1998 | Hilton et al. ................ | 345/156 |
| 5,736,102 A * | 4/1998 | Seaton et al. ................. | 422/65 |
| 5,905,205 A | 5/1999 | Clay | |
| 6,038,933 A * | 3/2000 | Meyer .................... | 73/862.045 |
| 6,058,784 A | 5/2000 | Carroll et al. | |
| 6,487,902 B1 | 12/2002 | Ghosh | |
| 6,606,918 B2 | 8/2003 | Day et al. | |
| 6,718,833 B2 | 4/2004 | Xie et al. | |
| 6,860,156 B1 | 3/2005 | Cavallaro et al. | |
| 7,051,600 B1 * | 5/2006 | Cavallaro et al. ...... | 73/862.041 |
| 7,204,160 B1 | 4/2007 | Sadegh et al. | |
| 7,437,954 B2 * | 10/2008 | Sakano .................. | 73/862.044 |
| 2008/0193334 A1 * | 8/2008 | Ryan et al. .................... | 422/65 |

* cited by examiner

*Primary Examiner*—Max Noori
(74) *Attorney, Agent, or Firm*—King & Schickli, PLLC (57) ABSTRACT

A uniaxially-driven controlled biaxial testing fixture includes a base, a first coupler mounted to the base, and a load input drive rack mounted for linear movement with respect to the base. A second coupler and a first specimen grip are both mounted to the load input drive rack. Second, third and fourth specimen grips are also mounted for linear movement with respect to the base. First, second and third drive mechanisms connect the load input drive rack to the second, third and fourth specimen grips. Together the four specimen grips are oriented to provide biaxial application of force to a test specimen.

20 Claims, 9 Drawing Sheets

500
UNIAXIALLY-DRIVEN CONTROLLED BIAXIAL TESTING FIXTURE

TECHNICAL FIELD

The present invention relates generally to testing equipment and, more specifically, to a uniaxially-driven controlled biaxial testing fixture for applying a biaxial load to a test specimen.

BACKGROUND OF THE INVENTION

Biaxial testing apparatus are used to control the load placed along varying axes of a test specimen for testing mechanical properties of metals, plastics, composites, wood, fabrics, elastomers and other materials. Examples of biaxial testing equipment may be found in, for example, U.S. Pat. No. 5,905,205 to Clay, U.S. Pat. No. 5,279,166 to Ward et al. and U.S. Pat. No. 7,204,160 to Sadi et al. The present invention relates to a relatively simple and inexpensive fixture that may be simply attached to a universal load frame capable of only uniaxial deformation in order to provide biaxial deformation at different pre-selected ratios. The different ratios are provided by utilizing different gear sets in the testing fixture.

SUMMARY OF THE INVENTION

In accordance with the purposes of the present invention as described herein, a uniaxially-driven controlled biaxial testing fixture is provided. The testing fixture comprises a base, a first coupler mounted to the base, a load input drive rack mounted for linear movement with respect to the base, a second coupler mounted to the load input drive rack and a first specimen grip mounted to the load input drive rack. The testing fixture also includes a second specimen grip mounted for linear movement with respect to the base. A first drive mechanism connects the load input drive rack to the second specimen grip. Still further, the testing fixture includes a third specimen grip mounted for linear movement with respect to the base. A second drive mechanism connects the load input drive rack to the third specimen grip. A fourth specimen grip is also mounted for linear movement with respect to the base. A third drive mechanism connects the load input drive rack to the fourth specimen grip.

The testing fixture also includes a test specimen receiver that is carried on the base. The test specimen receiver comprises a support ring and a series of projecting lugs forming an adapter or receiver for a heating gun. The attachment of the heating gun allows testing under high temperature conditions.

More specifically describing the invention, the first drive mechanism includes first and second driven racks mounted for linear movement with respect to the base and first and second pinions connecting the load input drive rack with the first and second driven racks. The testing fixture further includes a first mount connecting the second specimen grip to the first and second racks.

The second drive mechanism includes a third driven rack mounted for linear movement with respect to the base and a first gear assembly connecting the load input drive rack to the third driven rack. In addition a second mount connects the third specimen grip to the third driven rack.

The third drive mechanism includes a fourth driven rack mounted for linear movement with respect to the base and a second gear assembly connecting the load input drive rack to the fourth driven rack. A third mount connects the fourth specimen grip to the fourth driven rack.

The first specimen grip opposes the second specimen grip and the third specimen grip opposes the fourth specimen grip. The first and second specimen grips move along a first axis and the third and fourth specimen grips move along a second axis wherein the first and second axes are perpendicular to one another.

Still further describing the invention, a first guide rail is secured to the base. The load input guide rack includes a first guide channel received on the first guide rail. This allows the toad input guide rack to slide smoothly along the first guide rail.

The testing fixture farther includes second and third parallel guide rails secured to the base. The first driven rack includes a second guide channel received on the second guide rail and the second driven rack includes a third guide channel received on the third guide rail. This allows the first and second driven racks to slide smoothly along the second and third guide rails.

The test fixture further includes axially aligned fourth and fifth guide rails secured to the base. The third driven rack includes a fourth guide channel received on the fourth guide rail while the fourth driven rack includes a fifth guide channel received on the fifth guide rail. This arrangement allows for the smooth translational movement of the third and fourth driven racks along the fourth and fifth guide rails. The third and fourth grips are connected to these driven racks, In accordance with an additional aspect of the present invention the second and third drive mechanisms include identical gear sets in order to provide the same drive ratio. It should be appreciated, however, that the testing fixture includes multiple gear sets providing multiple gear ratios. Each of the multiple gear sets are interchangeably mounted in the second and third drive mechanisms. Accordingly, by selecting a particular gear set and mounting them in the second and third drive mechanisms, the operator can select the drive ratio and thereby provide controlled biaxial deformation of a test specimen at different pre-selected ratios as desired for any particular testing application.

In accordance with still another aspect of the present invention, a test specimen is provided for a biaxial testing fixture. The test specimen comprises a cruciform planar body including a center section, first and second opposing legs extending from the center section along a first axis and third and fourth opposing legs extending from the center section along a second axis. The first and second axes are perpendicular to one another. Further, each leg includes an enlarged mounting section at its distal end opposite the center section. The test specimen is also characterized by an aperture in each enlarged mounting section and a cavity provided in the center section at an intersection of the first and second axis.

The test specimen may further include a first notch in the center section between the first and third legs and a second notch in the center section between the second and third legs. In addition, the test specimen includes a third notch in the center section between the second and fourth legs and a fourth notch in the center section between the first and fourth legs.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings:

FIG. 1b is a front plan view similar to FIG. 1a illustrating the device in the fully closed position with no test specimen in the grips;

FIG. 5b is a detailed schematical cross section view showing the test specimen in place on the test specimen receiver and further illustrating the positioning of a nozzle of a heat gull to heat the test specimen during the testing procedure.

Reference will now be made in detail to the present preferred embodiment of the invention, an example of which is illustrated in the accompanying drawings.

DETAILED DESCRIPTION OF THE PREFERRED EMBODIMENTS OF THE INVENTION

Reference is now made to drawing FIGS. 1a, 1b, 1c, and 2 generally illustrating the uniaxially-driven controlled biaxial testing figure 10 of the present invention. The testing fixture 10 may be used in conjunction with load testing equipment such as an Instron Model 5582 Universal Materials Testing Machine to determine biaxial testing values for test specimens of substantially any desired solid material.

Figure 2:
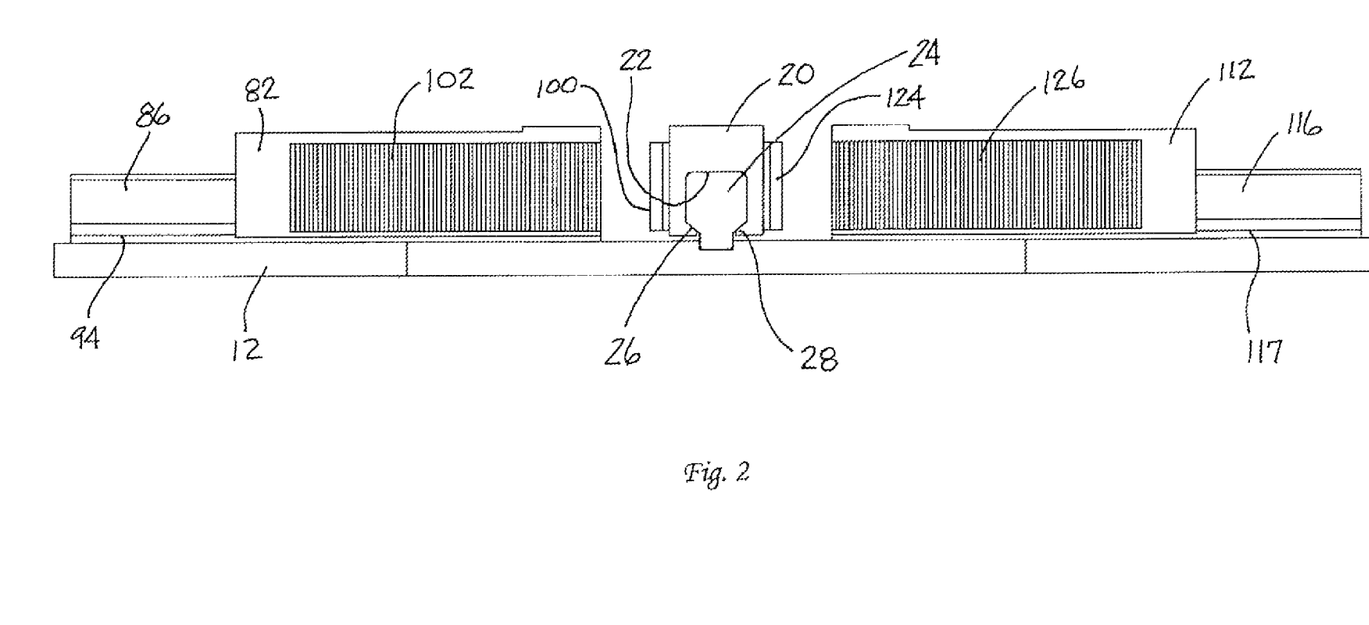
FIG. 2 is a detailed end elevational view of the load input drive rack showing the channel in the drive rack that is received over the first guide rail secured to the base of the device.

As illustrated, the testing fixture includes a base 12 which may be formed from a plate of steel or other appropriate high strength material. A first coupler 14 is mounted to a first end of the base 12 by means of a bracket 16 and appropriate fasteners 18. A load input drive rack 20 is mounted for linear movement with respect to the base 12. More specifically, as best illustrated in FIG. 2, the load input drive rack 20 includes a first guide channel 22 running along the length of the drive rack. A cooperating guide rail 24 is secured to the base 12 by welding, bolts or other appropriate fastening means. The guide rail 24 includes an undercut groove 26 on both sides at the bottom of the guide rail adjacent the base 12. The load input drive rack 20 fits on and slides along the guide rail 24. More specifically, the guide rail 24 is received in the guide channel 22 of the drive rack 20. Shoulders 28 on the drive rack 20 engage in the undercut grooves 26 of the guide rail 24 so that the drive rack is captured on the guide rail 24 but can freely slide on the guide rail as required during testing.

As further illustrated in FIGS. 1a, 1b, 1c and 2, a second coupler 30 is pivotally mounted to the load input drive rack 20 by means of the trunion 32 and cooperating pin 34. Still further, a first specimen grip 36 is mounted to the load input drive rack 20 by means of the stand 38. A nut and bolt fastener 40 secures the specimen grip 36 to the stand 38. Fasteners 42 secure the stand 38 to the load input drive rack 20.

Figure 1A:
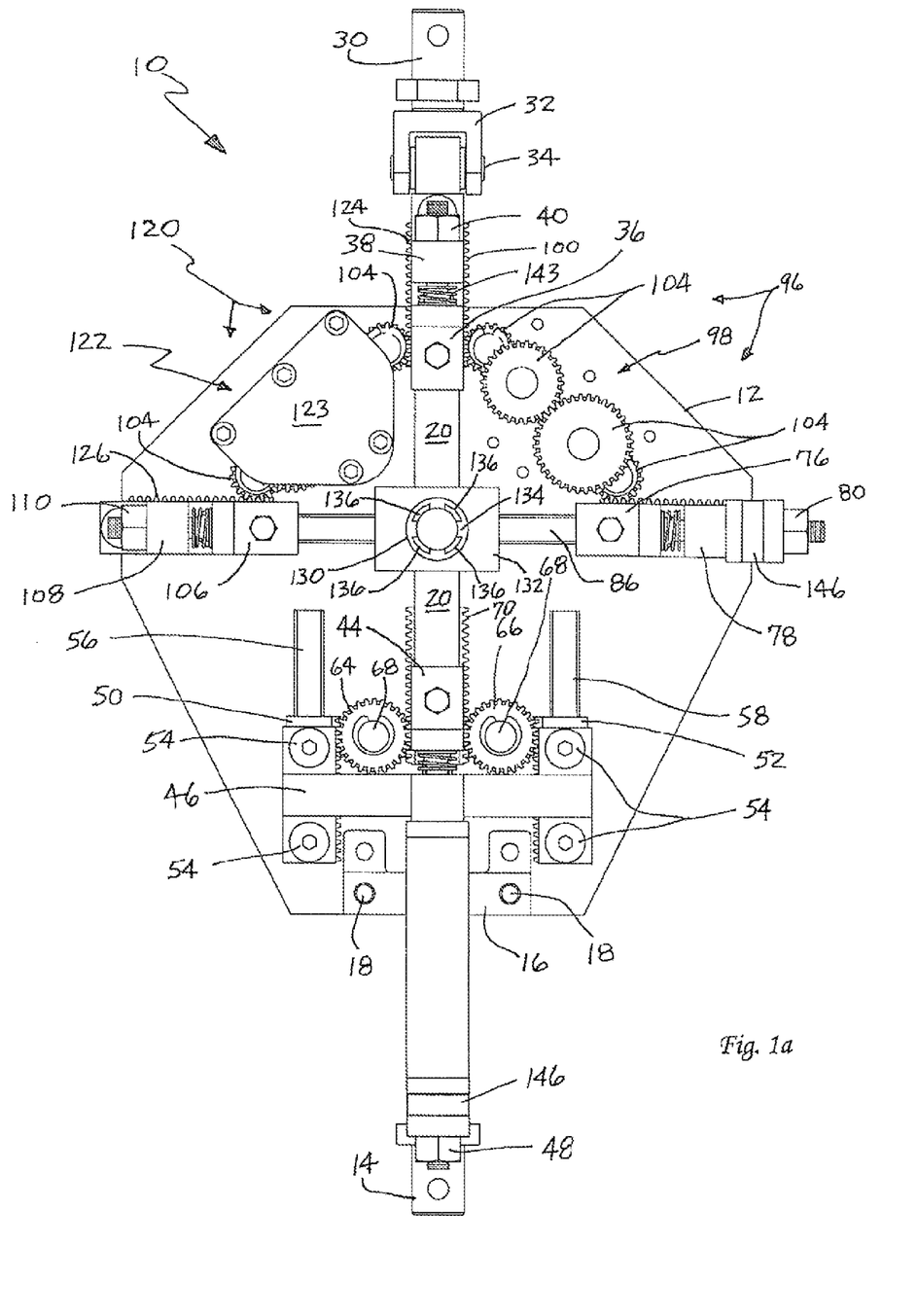
FIG. 1a is a front plan view illustrating the uniaxially driven controlled biaxial testing fixture of the present invention shown in the fully open or extended position with no test specimen held in the grips.
Figure 1C:
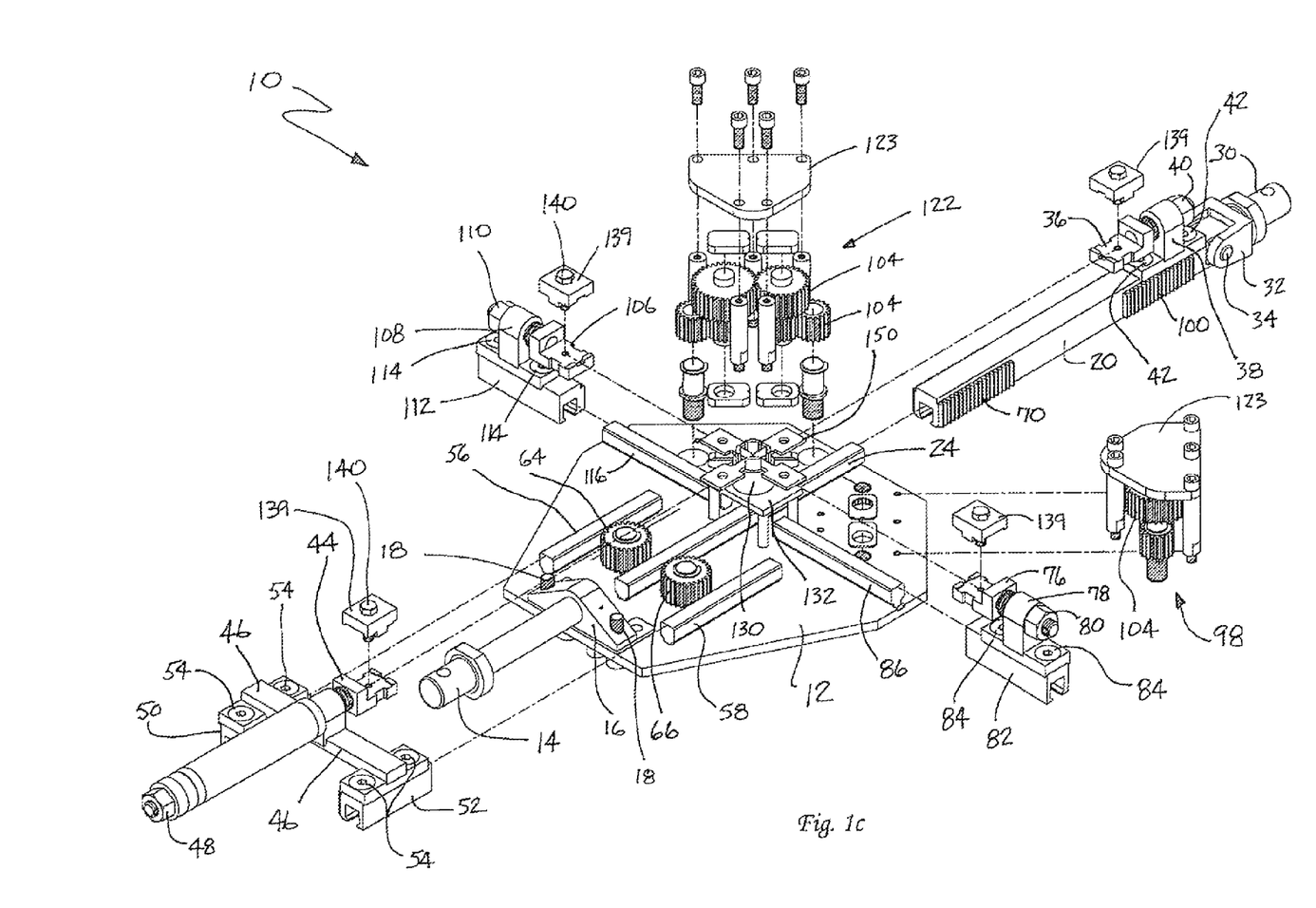
FIG. 1c is an exploded perspective view showing the device holding a test specimen on the specimen holder in the specimen grips.
Figure 3:
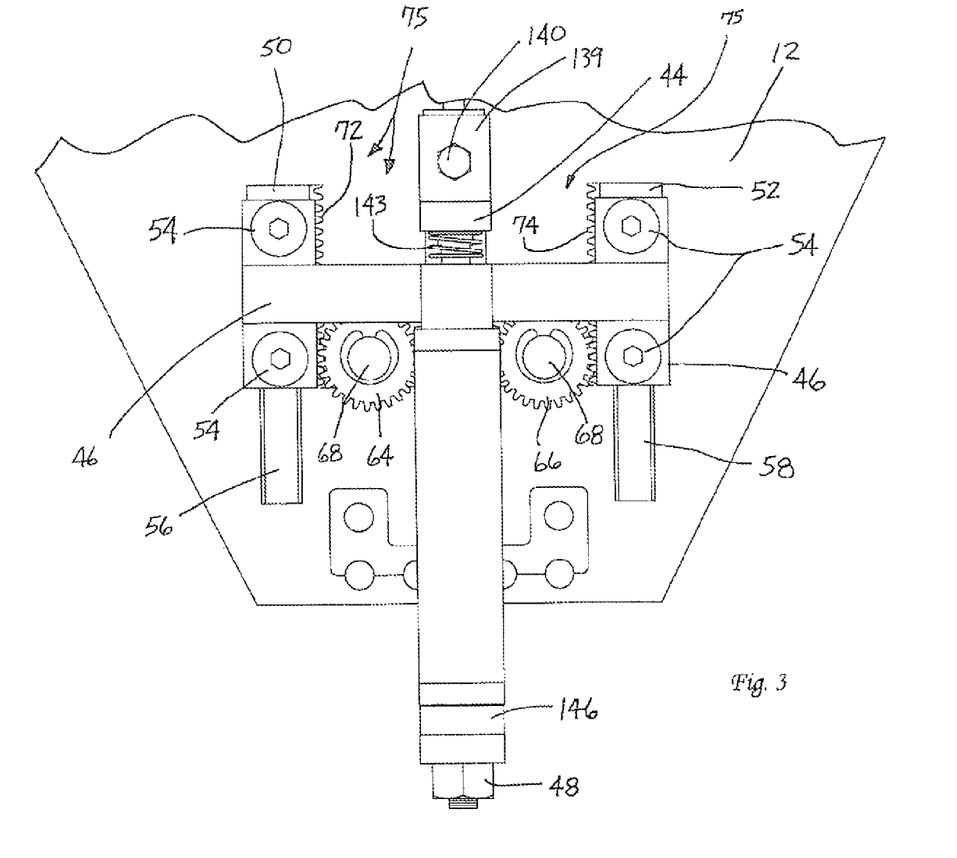
FIG. 3 is a detailed front elevational view of the first drive mechanism connecting the load input drive rack to the second specimen grip.

A second specimen grip 44 is mounted for linear movement with respect to the base 12 opposite the first specimen grip 36 (see FIGS. 1a, 1b and 3). The second specimen grip 44 is mounted to a stand or first mount 46 by means of a nut and bolt fastener 48. As illustrated, the first mount 46 is secured to first and second driven racks 50, 52 by fasteners 54. The first and second driven racks 50, 52 are secured for free sliding movement on second and third parallel guide rails 56, 58 secured to the base 12. Each of the guide rails 56, 68 includes undercut grooves (not shown) similar to those grooves 26 provided in the guide rail 24. Each of the first driven racks 50, 52 includes a guide channel (not shown) similar to the guide channel 22 of the load input drive rack 20. The guide rails 56, 58 are received in the guide channel of the driven racks 50, 52 and shoulders on the driven racks are received in the grooves in order to provide a free sliding connection.

First and second pinions 64, 66 are mounted for free rotation on stub shafts 68 secured to the base 12. The pinions 64, 66 connect the tooth rack 70 on the load input drive rack 20 with the tooth racks 72, 74 on the first and second driven racks 50, 52. Thus, the first and second driven racks 50, 52 and the first and second pinion 64, 66 form a first drive mechanism 75 that connects the load input drive rack 20 to the second specimen grip 44.

The testing fixture 10 also includes a third specimen grip 76 mounted on a stand or second mount 78 by means of fastener 80. The second mount 78 is secured to a third driven rack 82 by means of fasteners 84 (see FIGS. 1a, 1b and 4).

Figure 4:
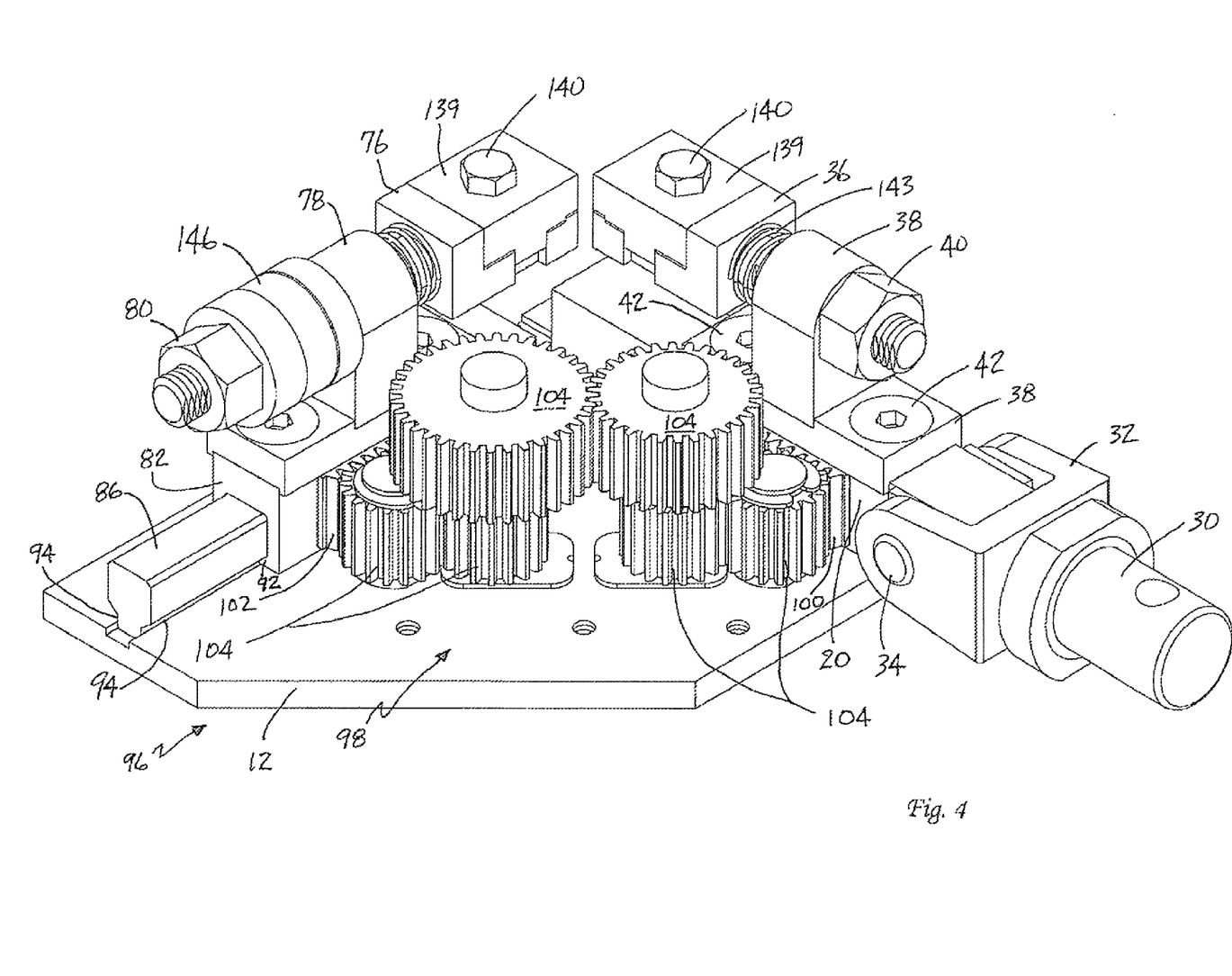
FIG. 4 is a detailed side elevational view of the second drive mechanism connecting the load input drive rack to the third specimen grip.

The third driven rack 82 is received for free sliding movement on a fourth guide rail 86 mounted to the base 12 by fasteners 88. More specifically, the third driven rack 82 includes a guide channel 90 that is received over the fourth guide rail 86 with shoulders 92 of the third driven rack received in cooperating opposed undercut grooves 94 in the fourth guide rail 86. A second drive mechanism, generally designated by reference numeral 96, connects the load input drive rack 20 to the third specimen grip 76. The second drive mechanism 96 includes the third driven rack 82 and a first gear assembly 98 that connects the tooth rack 100 on the load input drive rack 20 with the tooth rack 102 on the third driven rack 82. In the illustrated embodiment, the first gear assembly 98 comprises a series of six gears 104. It should be appreciated that the gear assembly 98 may comprise fewer or more than six gears as desired.

The testing fixture 10 also includes a fourth specimen grip 106 opposite the third specimen grip 76. The fourth specimen grip 106 is mounted to a stand or third mount 108 by means of a nut and bolt fastener 110. The third mount 108 is secured to a fourth driven rack 112 by means of fasteners 114. The fourth driven rack 112 is received on and freely slides with respect to a fifth guide rail 116. The fifth guide rail 116 is secured to the base 12 by means of fasteners 118. As should be appreciated, the fourth guide rail 86 and fifth guide rail 116 are axially aligned. The fourth driven rack 112 includes a guide channel (not shown) that is received over the guide rail 116. Opposed shoulders (not shown) on the driven rack 112 ride in cooperating undercut grooves 117 provided in the guide rail 116 in the manner described above with respect to shoulders 28 and grooves 26.

A third drive mechanism, generally designated by reference numeral 120, connects the load input drive rack 20 with the fourth specimen group 106. More specifically, the third drive mechanism 120 includes a second gear assembly 122 (partially hidden behind a plate 123) that connects the rack 124 on the load input rack 20 with the rack 126 on the fourth driven rack 112. In effect the third drive mechanism 120 is a mirror image of the second drive mechanism 96.

Like the first gear assembly 98, the second gear assembly 122 comprises a series of six gears 104. Each of the gear sets 104 of the assemblies 98 and 122 are identical. Advantageously, the testing figure 10 includes multiple gear sets providing multiple drive ratios. Each gear set 104 may be interchangeably mounted in the second and third drive mechanisms 96, 120. This allows the operator to provide controlled biaxial deformation to a test specimen at different pre-selected ratios. More specifically, the load provided on a test specimen between the first specimen grip 36 and second specimen grip 44 may be different than the load provided on the test specimen between the third specimen grip 76 and the fourth specimen grip 106. The ability to perform biaxial testing and simultaneously control the loading ratio of the test specimen along the two axes is a significant benefit of the present invention.

As further illustrated in FIGS. 1a, 1b, 1c and 5b, the testing fixture 10 also includes a test specimen receiver 130 mounted to the base 12 on a platform 132. As illustrated, the platform 132 straddles the load input drive rack 20.

The test specimen receiver 130 is cylindrical in shape and includes an upper shoulder comprising a support ring 134. A series of projecting lugs 136 axially extend from the support ring 134. As best illustrated in FIG. 5b, the lugs 136 are adapted to form a heating gun receiver. The purpose of this will be described in greater detail below.

Figure 6:
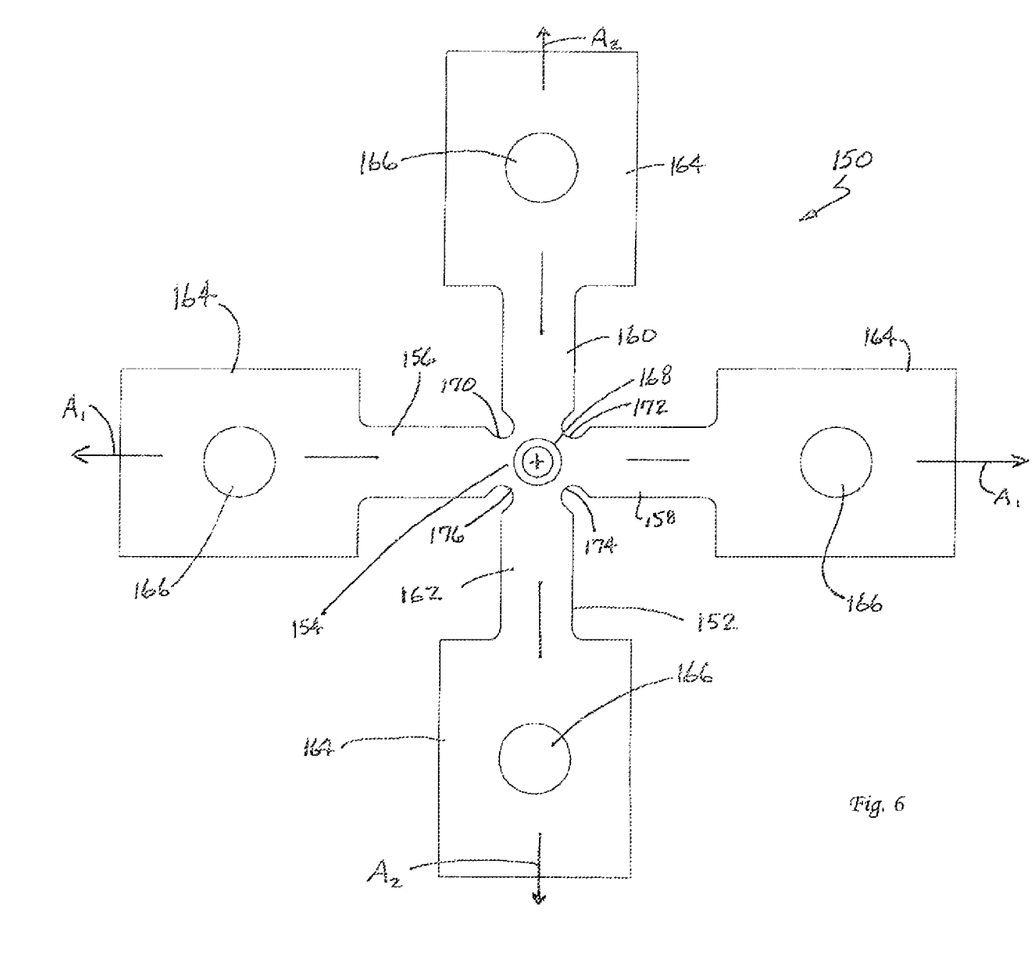
FIG. 6 is a top plan view of a test specimen.

As best illustrated in FIG. 6, each test specimen 150 comprises a cruciform planar body 152 including a center section 154 and four projecting legs 156, 158, 160 and 162. As illustrated, the first and second legs 156, 158 oppose one another and extend from the center section 154 along a first axis $A_1$. Similarly, the third and fourth legs 160, 162 oppose each other and extend from the center section 154 along a second axis $A_2$. The first and second axis $A_1$, $A_2$ are perpendicular to one another. As further illustrated, the distal end of each leg includes an enlarged mounting section 164 opposite the center section 154.

As further illustrated in FIG. 6, an aperture 166 is provided in each enlarged mounting section 164. In addition, a cavity 168 is provided in the center section 154 at an intersection of the first and second axes $A_1$ and $A_2$. In one possible embodiment, like aligned cavities 168 are provided in the opposite faces of the specimen 150 (see FIG. 5b). The cavity 168 may be formed by drilling or other means.

As further illustrated in FIG. 6, a notch 170 is provided in the center section 154 between the first leg 156 and third leg 160. A second notch 172 is provided in the center section 154 between the second leg 158 and third leg 160. A third notch 174 is provided in the center section 154 between the second leg 158 and the fourth leg 162. Finally, a fourth notch 176 is provided in the center section 154 between the first leg 156 and fourth leg 162.

The cavity 168 may have a diameter of between about 0.1875" and about 0.3125" and a depth of between about 0.0313" and about 0.0469". The notches 170, 172, 174, 176 may have a depth of between about 0.0884" and about 0.1326" and a width of about 0.0938" and about 0.125" so as to define a total surface of between about 0.0352 in$^2$ and about 0.0791 in$^2$. The cruciform planar body 152 of the test specimen 150 may have an overall thickness of between about 0.0938" and about 0.1563". This arrangement of notches 170, 172, 174, 176 and cavity 168 at the intersection of the axes $A_1$, $A_2$ guarantees the deformation taking place at the centre of the specimen, which is essential in claiming true biaxial deformation. Without this arrangement, deformation will not be concentrated at the centre of the specimen, and failure will eventually take place in one of the four legs.

When testing a test specimen 150, the test specimen is positioned with the center section 154 received within tie test specimen receiver 130. More specifically, the planar body 152 rests upon the support ring 134 with each of the legs 156, 158, 160, 162 extending in one of the four gaps 138 provided between each lug 136 (see FIGS. 5a and 5b).

Figure 5A:
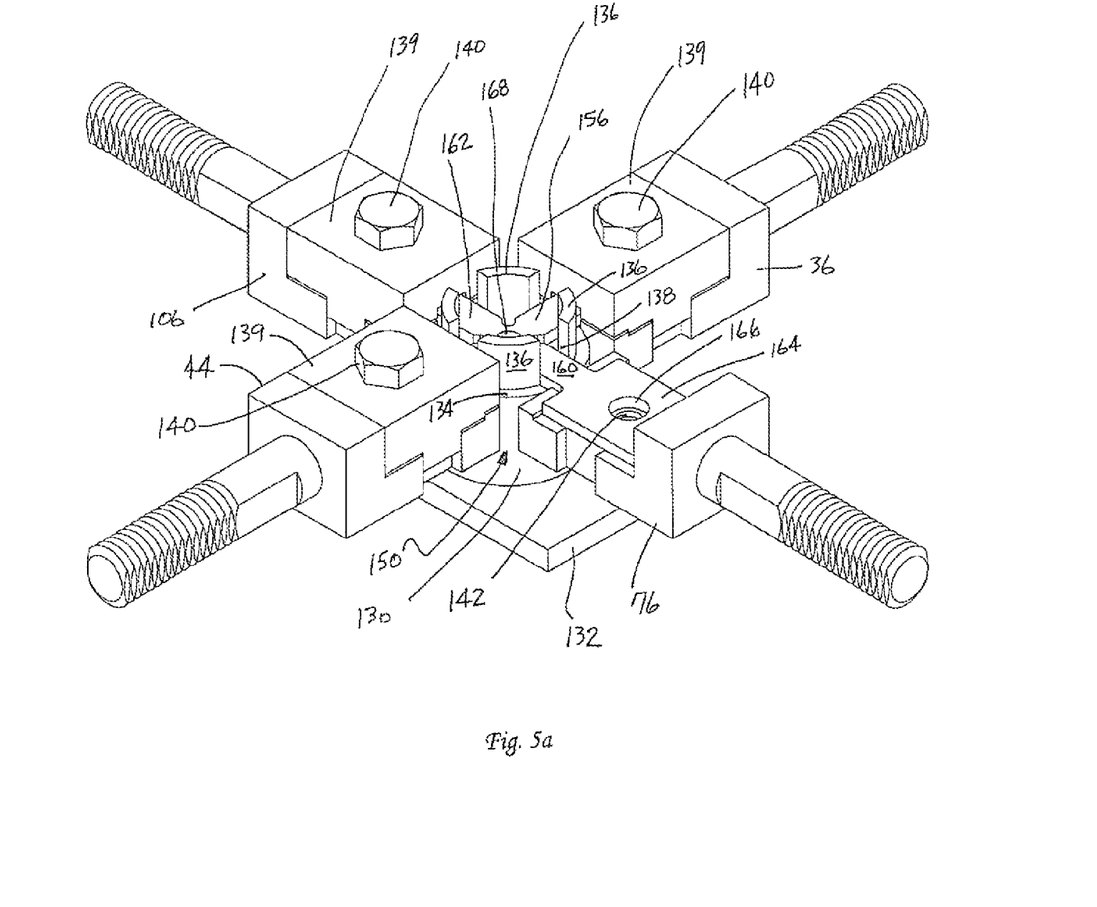
FIG. 5a is a detailed perspective view showing a test specimen held by the specimen grips on the test specimen receiver.

As best illustrated in FIGS. 5a and 5b, each specimen grip 36, 44, 76, 106 includes a clamping block 139 and a fastener 140. The fasteners 140 and clamping blocks 139 are removed and the distal ends 164 of the test specimen 150 are aligned on the grips 36, 44, 76, 106 so that the apertures 166 in the ends align with cooperating threaded apertures 142 in the grips. Tension springs 143 provided between each specimen grip 36, 44, 76, 106 and each associated stand 38, 46, 78, 108 allow some play for fine adjustment to insure that the apertures 166, 142 may be aligned.

If high temperature testing is desired, a heating gun G may be utilized to heat the test specimen 150 during testing. More specifically, as illustrated in FIG. 5b, the output end of the heating gun G is received on a cylindrical adapter 144 mounted to the lugs 136 projecting from the test specimen receiver 130. In this way heat from the gun G is provided directly to the test specimen 150. A thermocouple (not shown) may be mounted in the test specimen receiver 130 to monitor the test temperature.

For testing, the testing fixture 10 is connected to a universal materials testing machine. More specifically, the first coupler 14 is connected to the machine base while the second coupler 30 is connected to the crosshead beam. The universal materials testing machine is then actuated to apply a load to the test specimen 150 through the testing fixture 10. Load is applied on the first axis $A_1$ running through the opposed first and second specimen grips 36, 44: that is, along the axis of the load input drive rack 20. More specifically, as force is applied to the load input drive rack 20 that same force is directly applied to the first specimen grip 36 carried on the load input drive rack 20. Simultaneously, that force is also applied to the second specimen grip 44 through the first drive mechanism 75, the third specimen grip 76 through the second drive mechanism 96 and the fourth specimen grip 106 through the third drive mechanism 120. Load cells 146 allow one to directly monitor the testing. As different gear sets 128 with different ratios may be used in the testing fixture 10 for the first gear assembly 98 and second gear assembly 122, the ratio of force provided along the first axis $A_1$ between the first and second specimen grips 36, 44 and the second axis $A_2$ between the third and fourth specimen grips 76, 106 may be the same or different as desired to test the test specimen 150 for any particular application.

In summary, numerous benefits result from employing the concepts of the present invention. The testing fixture 10 is of relatively simple and inexpensive design. Advantageously, it may be attached to a universal load frame, capable only of uniaxial deformation to provide controlled biaxial deformation at different pre-selected ratios. The ability to conduct biaxial tests at different ratios using a relatively inexpensive uniaxial deformation load frame represents significant cost savings for the tester. Further, the ability to complete testing at elevated temperatures using a heating gun provides additional significant benefits, particularly when the test specimen is to be used in high temperature applications.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention ill various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A uniaxially-driven controlled biaxial testing fixture comprising:
   a base;
   a first coupler mounted to said base;
   a load input drive rack mounted for linear movement with respect to said base;
   a second coupler mounted to said load input drive rack;
   a first specimen grip mounted to said load input drive rack;
   a second specimen grip mounted for linear movement with respect to said base;
   a first drive mechanism connecting said load input drive rack to said second specimen grip,
   a third specimen grip mounted for linear movement with respect to said base;
   a second drive mechanism connecting; said load input drive rack to said third specimen grip;
   a fourth specimen grip mounted for linear movement with respect to said base; and
   a third drive mechanism connecting said load input drive rack to said fourth specimen grip.

2. The testing fixture of claim 1 further including a test specimen receiver carried on said base.

3. The testing fixture of claim 2, wherein said test specimen receiver comprises a support ring and a series of projecting lugs forming a heating gun receiver.

4. The testing fixture of claim 1, wherein said first drive mechanism includes, first and second driven racks mounted for linear movement with respect to said base and first and second pinions connecting said load input drive rack with said first and second driven racks.

5. The testing fixture of claim 4, further including a first mount connecting said second specimen grip to said first and second driven racks.

6. The testing fixture of claim 5, wherein said second drive mechanism includes a third driven rack mounted for linear movement with respect to said base and a first gear assembly connecting said load input drive rack to said third driven rack.

7. The testing fixture of claim 6, further including a second mount connecting said third specimen grip to said third driven rack.

8. The testing fixture of claim 7, wherein said third drive mechanism includes a fourth driven rack mounted for linear movement with respect to said base and a second gear assembly connecting said load input drive rack to said fourth driven rack.

9. The testing fixture of claim 8, further including a third mount connecting said fourth specimen grip to said fourth driven rack.

10. The testing fixture of claim 9, wherein said first specimen grip opposes said second specimen grip and said third specimen grip opposes said fourth specimen grip and said first and second specimen grips move along a first axis and said third and fourth specimen grips move along a second axis wherein said first and second axis are perpendicular to one another.

11. The testing fixture of claim 1, further including a first guide rail secured to said base.

12. The testing fixture of claim 11 wherein said load input guide rack includes a first guide channel received on said first guide rail.

13. The testing fixture of claim 12, further including second and third parallel guide rails secured to said base.

14. The testing fixture of claim 13, wherein said first driven rack includes a second guide channel received on said second guide rail and said second driven rack includes a third guide channel received on said third guide rail.

15. The testing fixture of claim 14, further including axially aligned fourth and fifth guide rails secured to said base.

16. The testing fixture of claim 15, wherein said third driven rack includes a fourth guide channel received on said fourth guide rail and said fourth driven rack includes a fifth guide channel received on said fifth guide rail.

17. The testing fixture of claim 1, wherein said second and third drive mechanisms include identical gear sets.

18. The testing fixture of claim 17, further including multiple gear sets providing multiple drive ratios, each of said multiple gear sets being interchangeably mounted in said second and third drive mechanisms.

19. A test specimen for a biaxial testing fixture, comprising:
   a cruciform planar body including a center section, first and second opposing legs extending from said center section along a first axis and third and fourth opposing legs extending from said center section along a second axis wherein said first and second axis are perpendicular to one another, each leg further including an enlarged mounting section at a distal end opposite said center section;
   said test specimen being characterized by an aperture in each enlarged mounting section and a cavity provided in said center section at an intersection of said first and second axis.

20. The testing specimen of claim 19, further including a first notch in said center section between said first and third legs, a second notch in said center section between said second and third legs, a third notch in said center section between said second and fourth legs and a fourth notch in said center section between said first and fourth legs.

* * * * *